(12) United States Patent
Egorov et al.

(10) Patent No.: US 8,069,735 B1
(45) Date of Patent: Dec. 6, 2011

(54) TACTILE SENSOR ARRAY FOR SOFT TISSUE ELASTICITY IMAGING

(75) Inventors: Vladimir Egorov, Princeton, NJ (US);
Armen P. Sarvazyan, Lambertville, NJ (US); Milind Patel, Bensalem, PA (US)

(73) Assignee: Artann Laboratories Inc., Trenton, NJ (US)

( * ) Notice: Subject to any disclaimer, the term of this patent is extended or adjusted under 35 U.S.C. 154(b) by 0 days.

(21) Appl. No.: 12/943,296

(22) Filed: Nov. 10, 2010

(51) Int. Cl.
*G01D 7/00* (2006.01)
*G01L 3/00* (2006.01)

(52) U.S. Cl. .............................. 73/862.046; 73/862.041

(58) Field of Classification Search ............ 73/862.046, 73/862.041; 438/125, 106; 257/700, 682; 341/33, 20, 22; 345/158, 168, 173; 200/600; 361/287

See application file for complete search history.

(56) References Cited

U.S. PATENT DOCUMENTS

| | | | |
|---|---|---|---|
| 3,978,508 A | 8/1976 | Vilkomerson | |
| 4,246,448 A | 1/1981 | Tam | |
| 5,760,530 A | 6/1998 | Kolesar | |
| 6,916,979 B2 | 7/2005 | Raisanen | |
| 7,216,417 B2 | 5/2007 | Raisanen | |
| 7,313,854 B2 | 1/2008 | Kim | |
| 7,430,925 B2 | 10/2008 | Son | |
| 7,481,120 B2 | 1/2009 | Gravesen | |
| 7,591,166 B2 | 9/2009 | Ueda | |
| 7,609,178 B2 | 10/2009 | Son | |
| 7,659,502 B2 | 2/2010 | Tachi | |
| 7,673,528 B2 | 3/2010 | Yoon | |
| 7,698,961 B2 | 4/2010 | Schostek | |
| 7,701,202 B2 | 4/2010 | Torres-Jara | |

*Primary Examiner* — Brian Szmal
(74) *Attorney, Agent, or Firm* — Boris Leschinsky (57) ABSTRACT

A tactile sensor array includes a first electrode layer and a second electrode layer with a two-phase compressible dielectric material therebetween. A ferroelectret film is used as a dielectric layer. In some embodiments, to improve sensor sensitivity and at the same time provide for high stability and reproducibility of sensor readings, the ferroelectret film is vented to atmosphere via a venting network of channels traversing at least one electrode layer and a curved rigid substrate. In some embodiments, an elastic supporting structure is provided that comprises individual elastic fastening elements connecting all layers of the sensor together. These individual elastic fastening elements are located throughout the layers of the sensor and prevent cross-talk between the individual sensors that may be caused by local shifts of parts of the sensor during use.

11 Claims, 5 Drawing Sheets

TACTILE SENSOR ARRAY FOR SOFT TISSUE ELASTICITY IMAGING

REFERENCE TO GOVERNMENT-SPONSORED RESEARCH

This invention was made with the U.S. government support under National Institutes of Health grant No. CA082620-0652 awarded by the National Cancer Institute. The government has certain rights in this invention.

BACKGROUND

The present invention relates generally to tactile sensors. More particularly, various embodiments of the invention describe novel tactile sensor arrays configured for elasticity imaging of soft tissue by recording a stress pattern on the tissue surface when a compression load is applied thereto.

Tactile imaging is a recently developed medical imaging technique used to improve upon and reduce the subjectivity in clinical palpation. It is used for external or internal evaluation of various soft tissues of the human body. In particular, tactile imaging is advantageous in objective evaluation of breast tissue for the presence of lumps. When a woman visits her physician, part of the physical exam often includes a clinician attempting to palpate the patient for any lumps or changes in the breast tissue that could indicate the presence of a tumor. This manual palpation method, however, only gives the physician a vague sense of what is actually underneath the skin. Due to the lack of any precise measuring device, if a lump is found through palpation, typically all that can be documented is its general location on the breast and a rough estimate of size.

To solve this problem, various tactile imaging systems have been proposed in the prior art by the inventors of the present invention as well as by others. A typical tactile imaging system consists of a hand-held device, referred to as a tactile probe, which replaces the physician's fingertips with an array of tactile sensors. When this tactile probe is used to compress the tissue, the contact pressure between the patient and the tactile probe is recorded by a computer. Simultaneously, an optional position tracker may be used to record the location of the probe such that the spatial distribution of the stress patterns can be recorded. Presence of lumps in the tissue can then be identified with high precision allowing a more informed clinical diagnosis to be made.

A typical tactile array of the tactile probe may be based on capacitance-measuring individual tactile sensors. Such sensors may be formed by providing a first electrode layer with rows of electrodes and a second electrode layer with columns of electrodes and a compressible dielectric layer therebetween. Individual sensors are formed in locations where rows of electrodes of the first electrode layer cross over columns of electrodes of the second layer. Monitoring capacitance of the sensors (such as for example by analyzing voltage between the electrode layers at each location of the sensor) allows recording of a stress pattern when the sensor is pressed against the tissue. Such tissue compression causes uneven compression of the dielectric layer which is translated into a number of capacitance measurements for respective sensors of the tactile array.

Using such technology for evaluation of the elasticity of the human tissue presents a number of unique challenges. One important requirement for a tactile probe is high consistency and reproducibility of results. The tactile sensor array of the tactile probe has to be designed to provide stable results despite variations of temperature or the method of probe handling which may somewhat change from one clinician to the next. Another important requirement is to provide a tactile probe with high sensitivity so as to detect even a faint difference in the tissue stress pattern which may be indicative of a small or deeply located tumor.

As can be appreciated by those skilled in the art, it is difficult to provide a tactile probe which is both highly sensitive and at the same time demonstrates repeatable and stable results as increasing sensitivity tends to cause an increase in artifacts and drifts caused by changing temperature or other environmental factors.

Ferroelectrets also known as piezoelectrets, are recently-developed thin films of polymer foams, exhibiting piezoelectric and pyroelectric properties after electric charging. Ferroelectret foams usually consist of a cellular polymer structure filled with air. Polymer-air composites are elastically soft due to their high air content as well as due to the size and shape of the polymer walls. Their elastically-soft composite structure is an essential key for the working principle of ferroelectrets, besides the permanent trapping of electric charges inside the polymer voids. The elastic properties allow deformations of the electrically charged voids. However, the composite structure can also possibly limit the stability and consequently the range of applications.

The most common effect related to ferroelectrets is the direct and inverse longitudinal piezoelectricity. In these cellular polymers, stress applied normally to the surface of the polymer film generally decreases the thickness of the sample. The thickness decrease occurs across the voids of the polymer causing to decrease the electrode charges. This effect makes ferroelectrets useful as a tactile sensor as they provide high sensitivity to applied pressure. At the same time, air presence makes ferroelectrets hard to work with as thermal expansion of microscopic air pockets causes the drift of the sensor reading.

SUMMARY

While both use of ferroelectret film for tactile sensing in non-medical settings and use of tactile sensors other than ferroelectret film in medical settings are known, it is believed that the present invention is the first to use ferroelectret film for tactile sensing in medical settings. As alluded to above, the sensitivity of ferroelectret-film-based tactile sensors would make them ideal for medical settings, but, until now, no one has been able to achieve an adequate level of stability and/or repeatability. Embodiments of the present invention provide ferroelectret-film-based tactile sensors that achieve a level of stability and/or repeatability to make such tactile sensors suitable for use in medical settings. Such sensors can be particularly beneficial when incorporated into a transrectal probe for purposes of tactile imaging of a patient's prostate.

Accordingly, it is an object of at least some embodiments of the present invention to overcome these and other drawbacks of the prior art by providing a novel tactile sensor array for a tactile probe with high sensitivity and high repeatability of results, the tactile probe being suitable for sensitive evaluation of human soft tissue.

It is another object of at least some embodiments of the present invention to provide a tactile sensor array with a compressible dielectric layer configured to measure impedance to represent the stress pattern applied to the sensor surface.

It is a further object of at least some embodiments of the present invention to provide a tactile sensor array suitable for elasticity imaging of human tissue in which the sensor array is assembled over a curved surface configured specifically for each type of soft tissue to be evaluated.

It is yet a further object of at least some embodiments of the present invention to provide a tactile sensor array which is easy and inexpensive to manufacture.

The tactile sensor array of at least some embodiments of the invention includes a thin two-phase compressible dielectric layer such as a ferroelectret film placed between the first electrode layer and the second electrode layer and assembled over a curved rigid substrate of the tactile probe. Applying compression using this probe results in a stress pattern imparted onto the ferroelectret layer. Electrode layers are used to measure impedance at various locations throughout the tactile sensor area and so the stress pattern is recorded as an electrical signal representing a changed impedance pattern over the sensor area.

To improve stability of results, the ferroelectret layer is vented over at least a portion or preferably its entire surface area to atmosphere by providing a venting network of channels. To further increase stability of results, various layers of the tactile sensor array of at least some embodiments of the invention are held together with an elastic supporting structure, in which individual fastening elements are spread out throughout the surface of the sensor. This design is aimed to prevent shifting in layers' position during use. Lifting of the tactile probe off the subject tissue allows the elastic supporting structure to move all layer of the tactile sensor back into initial position thereby restoring initial calibration and performance of the sensor array.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF PREFERRED EMBODIMENTS

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Figure 1:
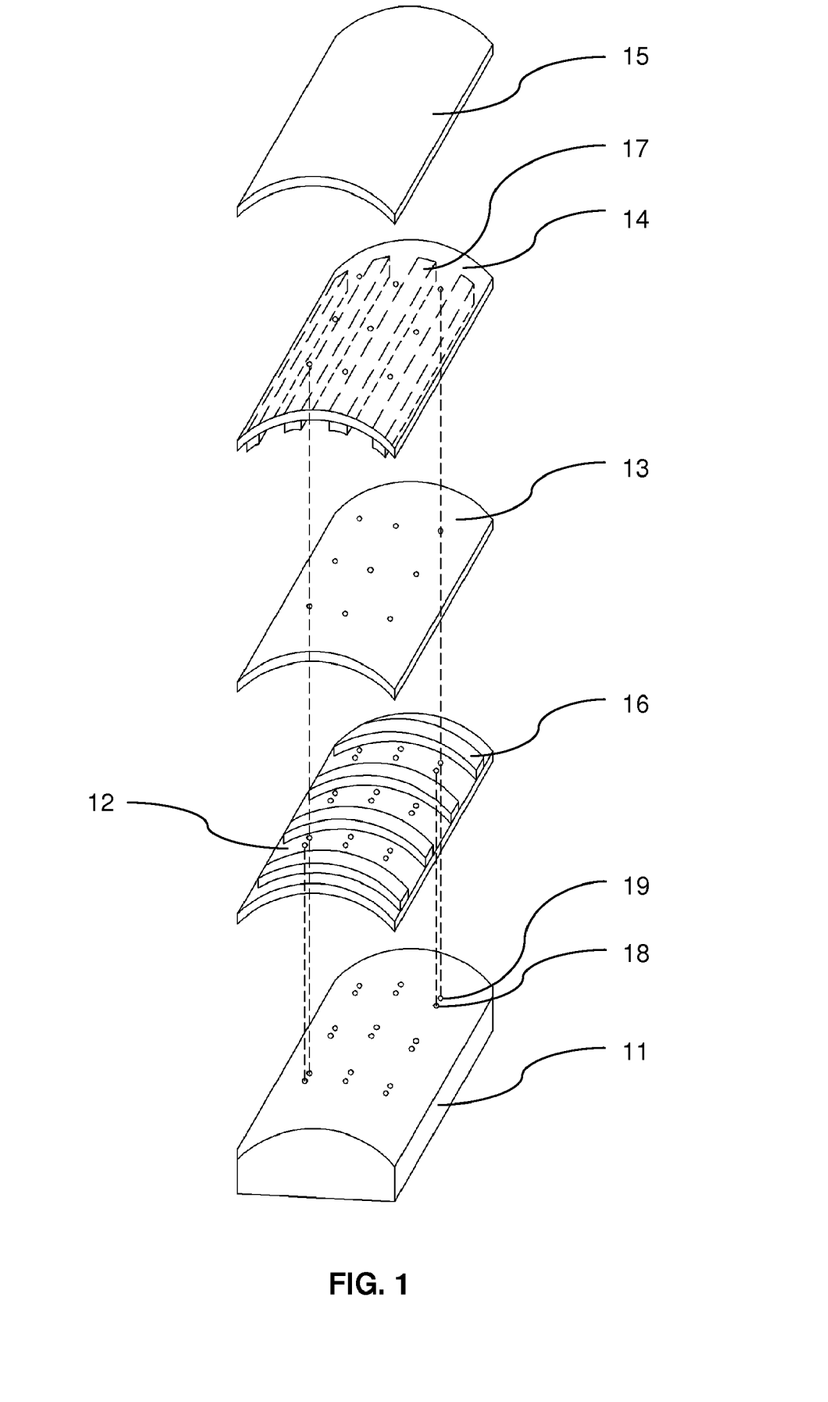
FIG. 1 is an exploded view of various components of the tactile sensor array of at least some embodiments of the present invention.
Figure 2:
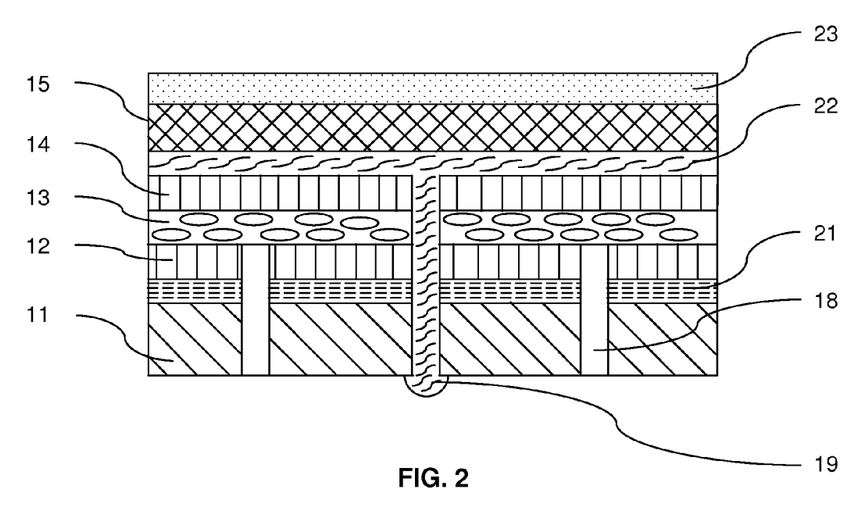
FIG. 2 is a cross-sectional side view of the tactile sensor array of FIG. 1 when assembled.

FIGS. 1 and 2 show the details of the tactile sensor array of at least some embodiments of the present invention. A rigid substrate 11 is provided with a curved surface onto which the tactile sensor array is assembled. The radius of curvature for the substrate 11 depends on a specific tissue to be studied. Softer tissues require higher radius of curvature. In general, the radius of curvature may vary from about 10 mm to about 50 mm to cover most soft tissues of interest for elasticity imaging. In some embodiments, the rigid substrate can be flat or not curved.

The first electrode layer 12 may be located in close contact with the curved surface of the substrate 11 and affixed thereto using for example contact cement 21 or another appropriate adhesive. The first electrode layer 12 may be a polyimide-based copper-plated single-sided flexible circuit with electrodes 16 formed for example by etching or another appropriate technique on one of its surfaces, such as the one facing the ferroelectret layer. Depending on the thickness of polyimide film, the reverse orientation of the electrode surface may also be used. The electrodes 16 may be optionally gold-plated and shaped in the form of parallel ridges forming columns of a sensor array matrix. Other shapes and forms of electrodes may also be used if appropriate.

Many design and environmental factors may influence sensor performance. During assembly or in operation, pockets of trapped air may be formed around the pressure-sensitive parts of the device. Such air pockets may cause sensor drift in situations where temperature or humidity may change from time to time. Increase in ambient temperature may cause the air pocket to expand and press onto the sensor causing it to drift. This is especially important in medical instruments. A medical instrument which includes a highly-sensitive tactile sensor has to exhibit higher degrees of accuracy, lack of drift and sensor sensitivity than is typically required of industrial sensors.

To address this issue, once the first electrode layer 12 is affixed onto the rigid substrate 11, a plurality of small diameter channels 18 and 19 are drilled through both elements. After the tactile sensor array construction is complete and the sensor surface is sealed, channels 18 form a venting network configured to provide atmosphere access to the ferroelectret film from the side of the first electrode layer 12 and the rigid substrate 11. Having a network of venting channels 18 avoids a problem of entrapped air pockets as described above. Any such volumes of air are no longer entrapped but are vented to atmosphere on a continuous basis. Channels 19 are used to form elastic supporting structure to hold all layers together as explained below in greater detail.

Channels 18 and 19 may be made throughout the surface of the first electrode layer 12, preferably (but not necessarily) at locations other than locations of electrodes 16. The size of the channels 18 and 19 should be small enough as to not allow deforming of the ferroelectret film or the electrode layer when pushed therein. In embodiments, the diameter of channels 18 and 19 ranges from about 0.05 mm to about 0.5 mm. The density of venting channels 18 is selected to preferably vent every sensor area to atmosphere. Assuming a rectangular matrix of sensors formed by rows and columns of electrodes, at least one venting channel 18 is placed in a center of the area including 4 to 12 individual sensors. In embodiments, the size of the sensor is selected to be 2 mm by 2 mm, therefore venting channels 18 may be spaced apart every 4-5 mm or so. Channels 19 are spaced apart in a similar manner—it is preferred to have at least one channel 19 for every 4 to 12 individual sensors.

A dielectric layer 13 may be located over the first electrode layer 12. A two-phase design of the dielectric layer 13 may be advantageous for the purposes of at least some embodiments of this invention. As opposed to a single-phase in which the entire dielectric layer is made from the same material, a two-phase dielectric layer may include a first phase such as a compressible polymer and a second phase such as voids filled with air or fluid. As the dielectric layer is compressed under load, the presence of the voids allow for local compression to take place without disturbing surrounding areas of the layer. Various foams and sponges may be cited as examples of a two-phase material in which a base material is filled with voids.

One advantageous example of a two-phase material suitable for use as a dielectric layer 13 of the sensor of at least some embodiments of the present invention is a ferroelectret film. The ferroelectret-based layer 13 may be a thin polyolefin film which is stretched or otherwise processed to include a plurality of voids filled with air. This film has a electrical sensitivity to compression from about 25 pC/N to about 250 pC/N. The thickness of the ferroelectret film may range from about 50 microns to about 150 microns, and preferably be about 70 microns. One particularly useful example of such film is a ferroelectret film produced by Emfit Ltd (Finland).

The second electrode layer 14 is located over the ferroelectret layer 13. The second electrode layer 14 may be made as a flexible circuit similar to that of the first electrode layer 12 with electrodes 17 etched on its surface and facing the ferroelectret film 13. Parallel ridges of electrodes 17 may be formed as rows of the final matrix in a direction perpendicular to electrode columns 16. Additional venting channels may be provided for the ferroelectret layer 13 on the side of the second electrode layer 14 although the design shown in FIG. 1 omits them and relies on venting of the ferroelectret layer 13 only from one side.

Assuming that the tactile sensor array contains at least two and preferably dozens or even hundreds of individual sensors, at least a first or a second electrode layer may contain a plurality of individual electrodes while the other electrode sensor may contain at least one or preferably many electrodes as well. Individual sensors are formed between the places where the electrodes of the first electrode layer overlay electrodes of the second electrode layer. Individual electrodes 16 and 17 are connected to an appropriate electronic control unit (not shown) configured to operate the tactile sensor array by measuring impedance or capacitance of each individual sensor.

Channels 19 are extended through all the tactile sensor array elements 11-14. They may be injected with a curable elastomer to form individual elastic fastening elements of the elastic supporting structure. In embodiments, one- or two-part silicone material may be used as such elastomer. The elastic nature of the supporting structure may be described by the Young's modulus of the material to be from about 100 kPa to about 10 MPa. The lower end of the range is selected to prevent rupture of the material when the sensor is in use. The upper end of the range is selected to exclude rigid materials so as to provide flexibility and allow for appropriate strain of sensor layers during use.

Tactile probes using the sensor array of this invention are used to apply mechanical pressure onto the subject of evaluation. As there is a lot of interaction between the sensor array and the subject, lateral movement of one against the other may cause a shift in the various layers of the sensor array. Such shift may cause an erroneous reading from the sensor array elements. In addition and particularly for medical instruments, it is preferred that the sensor array is calibrated once during production and does not require recalibration prior to every use. Small lateral shifts between the layers of the sensor may introduce a permanent error unless frequent calibration is performed.

The elastic supporting structure serves to mechanically bind all the layers of the tactile sensor together to provide stability and improved reproducibility of the sensor data. Importantly, the elastic supporting structure holds the layers together at a plurality of locations spread over the surface of the sensor. Closely spaced locations of channels 19 allow consistent retention of electrodes 16 and 17 next to the ferroelectret layer 13 throughout the surface of the sensor. During use, local shifts of portions of the layers are prevented from distorting the results of the tissue evaluation. The presence of elastic supporting structure allows avoiding frequent recalibration of the sensor and assures its accuracy and stability of operation over its entire lifetime of use.

The top protective ground layer of the tactile sensor array assembly is a thin and elastic electrically-conductive layer 15 configured to provide both mechanical protection and electric shielding from external capacitive and electromagnetic interference when connected to an electrical ground. Its flexibility and thickness are selected so as to avoid mechanical interference with the sensing function of the sensor assembly. In embodiments, layer 15 may be a soft bi-directionally elastic high-performance silver mesh fabric with surface resistivity of less than 0.5 ohm/sq. Any suitable electro-conductive fabric may be used for electrical shielding and mechanical protection purposes. It is preferred that the electro-conductive fabric is selected to be as thin as possible so as to add minimum weight to the tactile sensor array and is stretchable in two directions. The top protective layer 15 may be affixed to the second electrode layer 14 using the same elastomeric adhesive (shown as item 22 in FIG. 2) or using another flexible adhesive.

An optional additional protective elastic cover 23 is used to seal the entire tactile sensor array to prevent it from wear and tear. It also allows dipping the tactile sensor array in various disinfection and sanitization liquids without the risk of damaging the sensor. The elastic cover 23 may be made from polyurethane, PVC, PMMA or any other suitable material. It is preferred to have the cover 23 to be as thin and as flexible as possible to avoid any reduction in the tactile sensor sensitivity.

Figure 3:
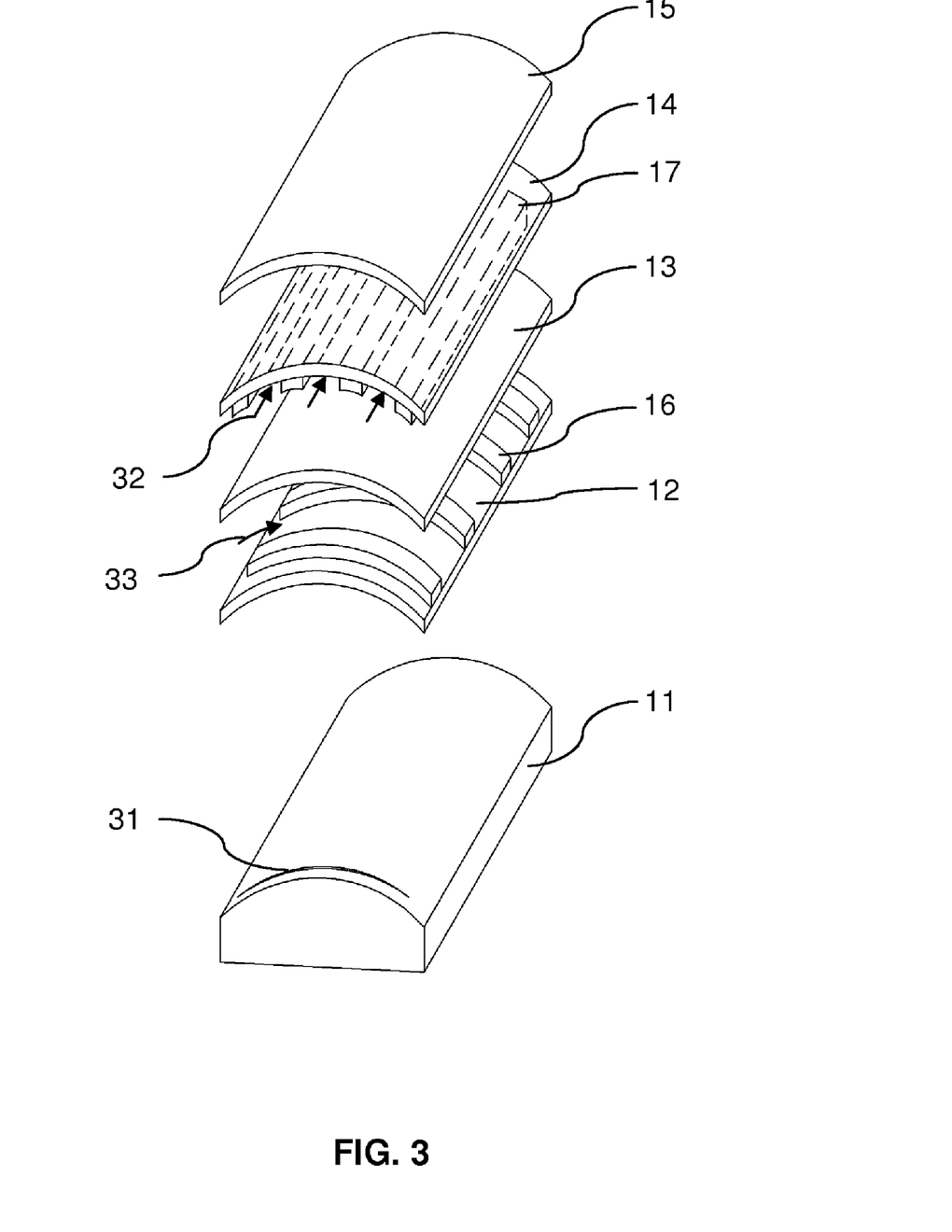
FIG. 3 shows a venting network of channels configured to vent the ferroelectret layer of the sensor array to atmosphere.

FIG. 3 shows an alternative design for the venting network of the ferroelectret layer. This design involves introducing a slit 31 extending all the way through the rigid substrate 11. Small venting channels 32 and 33 are created, respectively, in-between the electrodes 16 and 17 of the first and second electrode layers 12 and 14. Air vent is provided through the slit 31 and the network of channels 32 and 33 so as to allow venting of the ferroelectret layer 13. Electro-conductive fabric 15 may still be adhered to the flexible circuit 14 using an elastomer. Placement of the protective elastic cover 23 on top of the assembly will make the assembly airtight from the top.

At the same time, slit 31 provides air access to the tactile sensor array from the other side of the rigid substrate 11.

Figure 4:
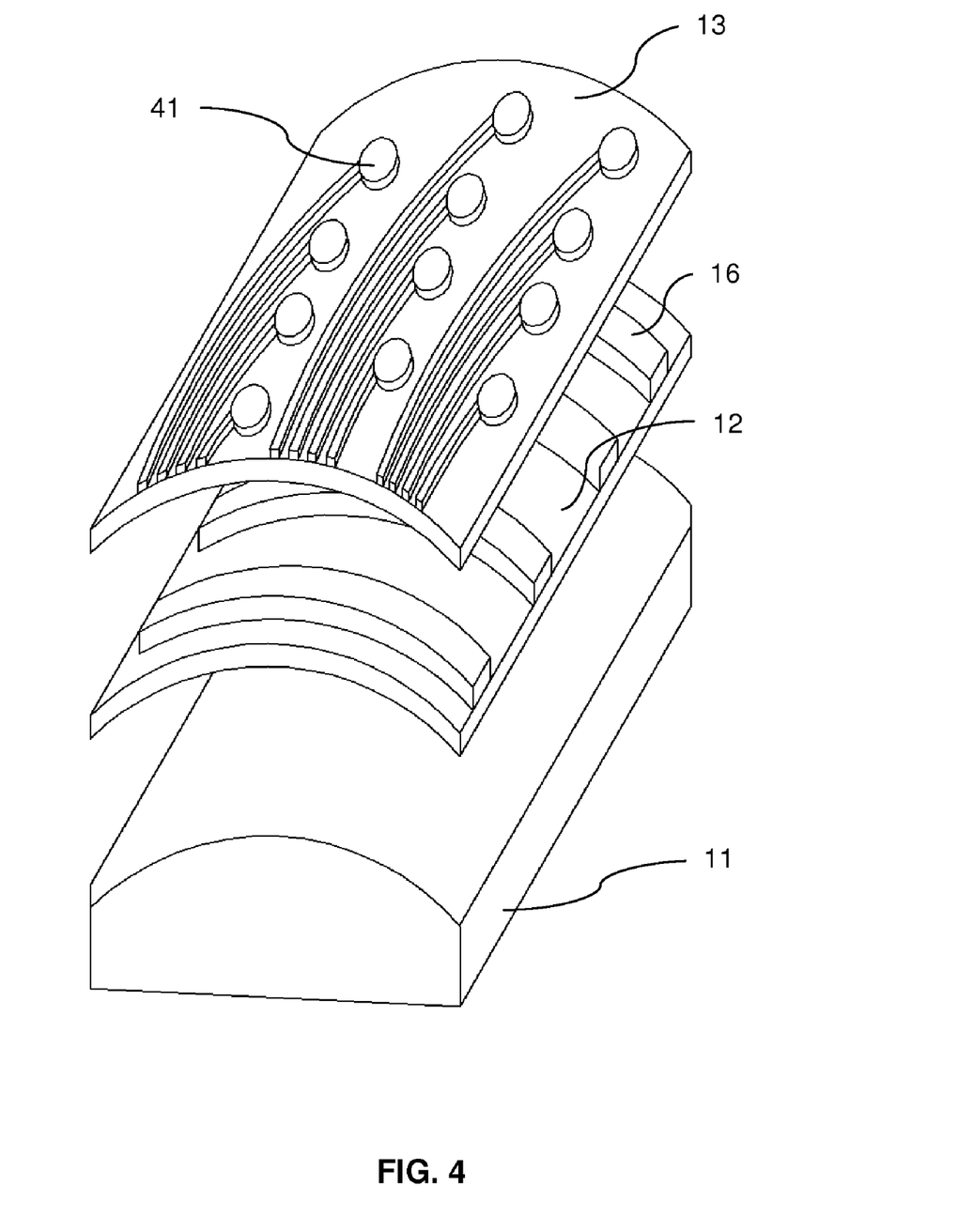
FIG. 4 shows a tactile sensor array in which at least some electrodes of the sensor array are deposited directly on the ferroelectret layer.

FIG. 4 shows an alternate design of the tactile sensor array when at least some electrodes of the first or the second electrode layers are directly deposited on the ferroelectret film. In the example shown in FIG. 4, electrodes 41 of the second electrode layer (with their respective conductors) are directly placed onto the ferroelectret film 13. One of the following deposition techniques may be used for that purpose:

a) a pulsed laser technique,
b) a sputtering method,
c) an electrophoretic deposition technique,
d) a self-limiting film growth mechanism,
e) an electrochemical deposition technique.

The rest of the sensor assembly is similar to what is described above.

In operation, the tactile sensor array may be activated by an AC generator with the amplitude in the range 2-20 V and frequency in the range from 100 kHz to 500 kHz. Each sensor is supplied with a predetermined voltage. In response to applied pressure, a change in impedance for each sensor is detected. This approach increases the signal-to-noise ratio. The output measured value for the tactile sensor array may be DC or AC voltage or current. The detection circuitry may include a multiplexer to poll sensors one at a time—individually or in groups.

Tactile sensor arrays as discussed herein can be incorporated into various medical instruments. For example, in embodiments of the present invention, one or more tactile sensor arrays can be incorporated into a probe to obtain a tactile image of breast tissue. In another example, a probe with tactile sensor array of the invention may be configured and sized for evaluation of pelvic floor organs and tissues. The medical instrument can include a rigid substrate over which a tactile sensor array can be placed. Such a medical instrument can enable an operator (e.g., a physician) to examine a patient. In this way, embodiments of the tactile sensor array discussed herein can be adapted for use in medical applications.

Figure 5A:
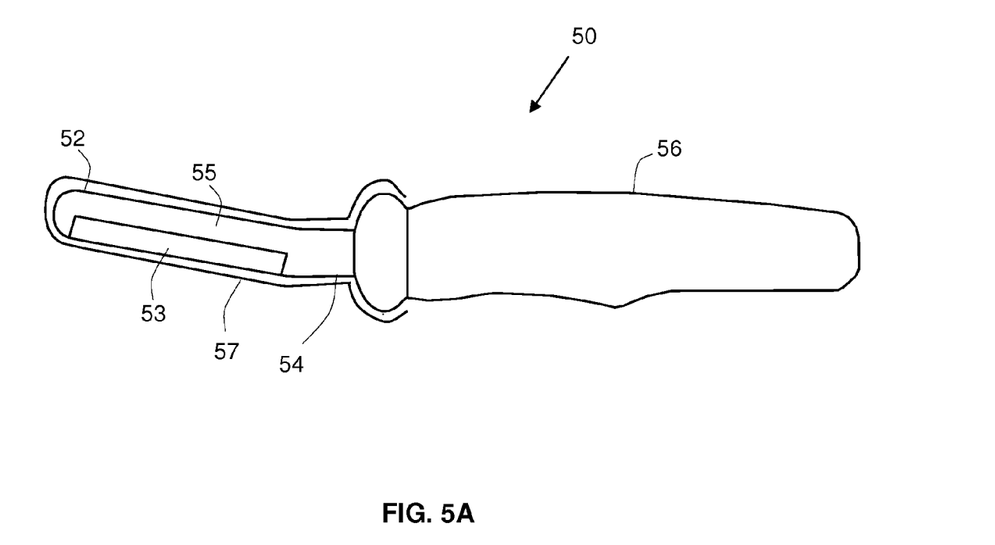
FIGS. 5A and 5B illustrate examples of a medical instrument using a tactile sensor array of the invention.
Figure 5B:
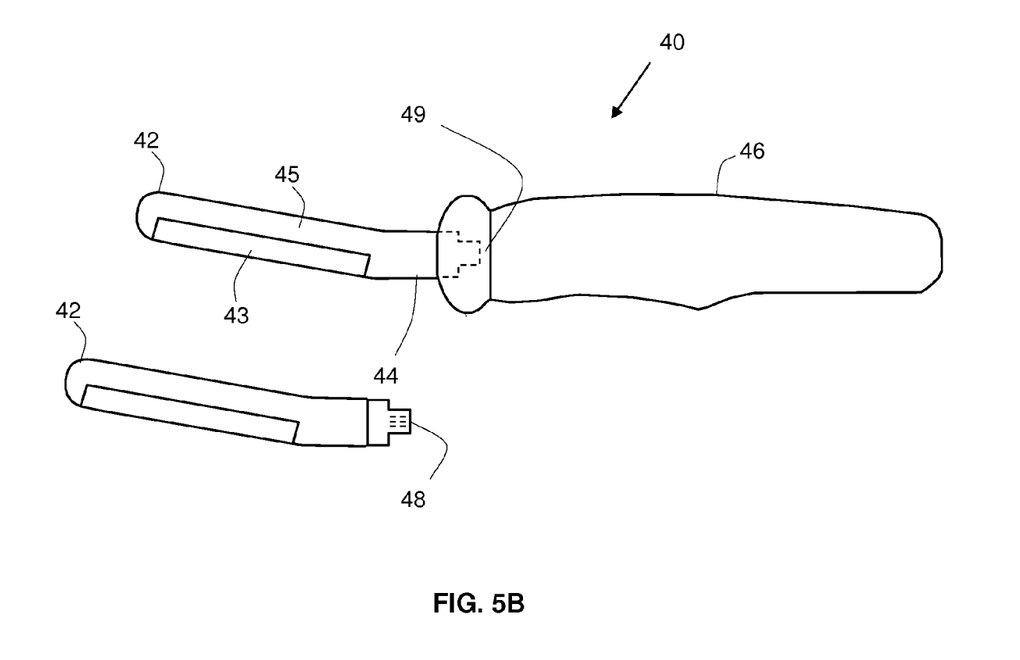

In preferred embodiments, tactile sensor arrays as discussed herein can be incorporated into transrectal probes for tactile imaging of patients' prostates. Such an embodiment is shown in FIGS. 5A-5B. As can be seen, the transrectal probe 50 includes a handle 56, a shaft 54 attached to (e.g., integral with) a distal end of the handle 56, and a head 52 attached to (e.g., integral with) a distal end of the shaft 54. The head 52 can include a rigid substrate 51 over which the tactile sensor array 53 can be placed. In this way, many of the advantages provided by the tactile sensor array 53, as discussed herein, can be realized in the context of prostate examination.

Transrectal probes for tactile (or mechanical) imaging of patients' prostates, and associated methods of use, are described in U.S. Pat. Nos. 7,819,824 (Method and a Dual-array Transducer Probe for Real Time Mechanical Imaging of Prostate), 6,569,108 (Real Time Mechanical Imaging of the Prostate), 5,785,663 (Method and Device for Mechanical Imaging of the Prostate), 5,265,612 (Intracavity Ultrasonic Device for Elasticity Imaging), 5,524,636 (Method and Apparatus for Elasticity Imaging), 5,836,894 (Apparatus for Measuring Mechanical Parameters of the Prostate and for Imaging the Prostate Using Such Parameters), 6,142,959 (Device for Palpation and Mechanical Imaging of the Prostate), and 5,922,018 (Method for Using a Transrectal Probe to Mechanically Image the Prostate Gland), as well as U.S. Patent Application Publication No. 2009/0005707 (Method and Device for Real Time Mechanical Imaging of Prostate), all of which are hereby incorporated by reference in their entirety.

In use, the shaft 54 and the head 52 are inserted into a patient's rectal canal to palpate the patient's prostate. The transrectal probe 50 of FIG. 5A includes a thin and flexible disposable cover 57 that envelops the head 52, the shaft 54, and in some cases part of the handle 56 in order to prevent contact between those components and the patient, thereby enabling multiple uses of the transrectal probe 50.

In the transrectal probe 40 of FIG. 5B, both the head 42 and the shaft 44 are detachable from the handle 46. The head 42 may include a tactile sensor array 43 placed over a rigid substrate 45. The proximal end of the shaft 44 can include a shaft connector 48, which can mate with a handle connector 49 in the distal end of the handle 46. Mating of the shaft connector 48 and the handle connector 49 can provide both mechanical and electrical (e.g., to provide electrical signal exchange between the tactile sensor array 43 and electronics housed in the handle 46) connection between the shaft 44 and the handle 46. In this way, after the probe 40 is used, the head 42 and the shaft 44 can be detached from the handle 46 and disposed of, and a new head 42 and shaft 44 can be attached to the handle 46, thereby enabling multiple uses of the handle 46 (and electronics housed therein).

As alluded to above, tactile imaging of the prostate involves the tactile sensor array 43 providing electrical signals to electronics housed in the handle 46. The electrical signals are representative of the stress pattern of the portion of the prostate being examined. The location of the tactile sensor array 43, and even the location of the individual sensors, can be tracked during examination as well. Electronics (in the handle 46 or upstream of the handle 46) can generate images based on the stress pattern data and the location data. Physicians can use such images to assess the condition of the patient's prostate. Thus, it is important that the stress pattern data be as precise and accurate as possible. Many of the tactile sensor arrays discussed herein can significantly improve the precision and accuracy of stress pattern data without sacrificing stability or repeatability.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A tactile sensor array comprising:
   (a) a first electrode layer including a first plurality of electrodes,
   (b) a second electrode layer including at least a second electrode, and
   (c) a two-phase dielectric layer located between said first electrode layer and said second electrode layer, said two-phase dielectric layer separating said first plurality of electrodes from said at least second electrode to form individual sensors of said tactile sensor array, said two-phase dielectric layer including a compressible material with a plurality of voids therein,
   wherein at least one of said first electrode layer or said second electrode layer contains a venting network of channels to connect at least one corresponding side of said dielectric layer to atmosphere.

2. The tactile sensor array as in claim 1, wherein said two-phase dielectric layer is a ferroelectret film.

3. The tactile sensor array as in claim 1 further including a curved rigid substrate, said first electrode layer, said two-phase dielectric layer and said second electrode layer placed over a curved part of said rigid substrate to assume a curved shape thereof.

4. The tactile sensor array as in claim 3 wherein said venting network of channels is traversing through said rigid substrate.

5. The tactile sensor array as in claim 3 further including an electrically-conductive elastic ground layer positioned above said second electrode layer to protect said tactile sensor array from mechanical and electromagnetic interference.

6. The tactile sensor array as in claim 1 wherein said venting network of channels is spaced over at least a portion of said two-phase dielectric layer and includes individual venting channels, each venting channel serving adjacent individual sensors of said tactile sensor array in groups of 4 to 12 per channel.

7. The tactile sensor array as in claim 1, wherein said venting network of channels are at least in part formed between and along electrodes of said first electrode layer or said second electrode layer.

8. A tactile sensor array comprising:
  (a) a first electrode layer including a first plurality of electrodes,
  (b) a second electrode layer including at least a second electrode,
  (c) a compressible dielectric layer located between said first electrode layer and said second electrode layer, said dielectric layer separating said first plurality of electrodes from said at least second electrode whereby individual sensors of said tactile sensor array are formed at location of overlap of said first and said second electrode layers, and
  (d) an elastic supporting structure including a plurality of individual elastic fastening elements, whereby said first electrode layer is attached to said compressible dielectric layer and further attached to said second electrode layer via said plurality of individual elastic fastening elements.

9. The tactile sensor array as in claim 8, wherein said individual elastic fastening elements are located throughout said tactile sensor array and in-between said individual sensors thereof.

10. The tactile sensor array as in claim 9, wherein each of said individual elastic fastening elements located next to a group of adjacent individual sensors.

11. The tactile sensor array as in claim 10, wherein said group includes between four and twelve individual sensors.

* * * * *